United States Patent
Svatos

(10) Patent No.: US 6,285,969 B1
(45) Date of Patent: Sep. 4, 2001

(54) USE OF SINGLE SCATTER ELECTRON MONTE CARLO TRANSPORT FOR MEDICAL RADIATION SCIENCES

(75) Inventor: Michelle M. Svatos, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/083,455

(22) Filed: May 22, 1998

(51) Int. Cl.$^7$ .............................. G06N 7/00; G05B 17/00
(52) U.S. Cl. ........................ 703/2; 703/5; 703/12
(58) Field of Search ......................... 703/2, 5, 12

(56) References Cited

U.S. PATENT DOCUMENTS

| | | | |
|---|---|---|---|
| 5,341,292 | 8/1994 | Zamenhof | 364/413.13 |
| 5,870,697 | * 2/1999 | Chandler et al. | 702/179 |
| 6,029,079 | * 2/2000 | Cox et al. | 600/407 |

FOREIGN PATENT DOCUMENTS

WO 97/32630  9/1997  (WO).

OTHER PUBLICATIONS

Smith, L. M. et al. "Accelerating Execution of the Integrated TIGER Series Monte Carlo Radiation Transport Codes," IEEE Transactions on Nuclear Science. vol. 44, No. 1, Feb. 1997, pp. 36–41.*

Hartmann et al, "Peregrine: an all–particle monte carlo code for radiation therapy," Proceeding of the International Conference on Mathematics and Computations, Reactor Physics and Environmental Analysis, vol. 2, Apr. 30, 1995–May 4, 1995, pp. 857–856, XP002083804.

Svatos et al, "Electron transport in radiotherapy using local––to–local monte carol," Proceedings of the International Conference on Mathematics and Computations, Reactor Physics and Environmental Analysis, vol. 2, Apr. 30, 1995–May 4, 1995, pp. 867–875, XP002083805.

* cited by examiner

Primary Examiner—Tariq R. Hafiz
Assistant Examiner—Kyle J. Choi
(74) Attorney, Agent, or Firm—John P. Wooldridge; Alan H. Thompson

(57) ABSTRACT

The single scatter Monte Carlo code CREEP models precise microscopic interactions of electrons with matter to enhance physical understanding of radiation sciences. It is designed to simulate electrons in any medium, including materials important for biological studies. It simulates each interaction individually by sampling from a library which contains accurate information over a broad range of energies.

2 Claims, 7 Drawing Sheets

--- finding the distance to interaction by finding the total cross section at the present energy and using the relation $s = -\lambda \ln(\eta)$, where $\eta$ is a random number on the interval $(0,1)$

↓ determining which type of atom in the material the interaction involved, knowing the ratio of chemical elements that comprise the material

↓ determining which interaction took place, by forming and sampling from a cumulative probability based on the LLNL Evaluated Electron Data Library doubly differential cross sections for each of the four possible interaction (ionization, excitation, elastic scatter, bremsstrahlung)

↓ updating the energy, position and trajectory of the particle to reflect the chosen interaction

↓ repeating the above steps until the electron has escaped the medium or fallen below the energy cutoff

USE OF SINGLE SCATTER ELECTRON MONTE CARLO TRANSPORT FOR MEDICAL RADIATION SCIENCES

RELATED APPLICATIONS

Copending U.S. Pat. No. 5,870,697, titled "Calculation of Radiation Therapy Dose Using All Particle Monte Carlo Transport" is fully incorporated herein by reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to radiation therapy, and more specifically it relates to a method for modeling the precise microscopic interactions of electrons with matter to enhance physical understanding of radiation sciences.

2. Description of Related Art

Currently in the United States, radiation therapy is used to treat about 60% of all cancer patients. Since radiation therapy targets specific areas of the body, improvement in radiation treatment techniques has the potential to reduce both mortality and morbidity in a large number of patients.

The radiation source may be in the form of external beams of ionizing particles or radioactive sources internal to the patient. External beams are usually produced by machines acting as particle accelerators. The beam delivery system consists of the radiation source, which is mounted on a gantry which can rotate about a 360° arc around the patient. Each beam is shaped by a rotatable collimator. The patient lies on a rotatable table. The gantry and table both rotate about a single isocenter.

External beam radiation therapy is performed with several types of ionizing radiation. Approximately 80% of patients are treated with photons, ranging in maximum energy from 250 keV to 25 MeV. The balance are treated primarily with electrons with energies from 4 to 25 MeV. In addition, there are several fast neutron and proton therapy facilities which have treated thousands of patients worldwide. Fast neutron therapy is performed with neutron energies up to 70 MeV, while proton therapy is performed with proton energies ranging from about 50 to 250 MeV. Boron neutron capture therapy is conducted with thermal and epithermal neutron sources. Most internal radioactive sources irradiate the patient with photons, although some sources emit low energy electrons.

The effects of ionizing radiation on the body are quantified as radiation dose. Absorbed radiation dose is defined as the ratio of energy deposited to unit mass of tissue. Because tumors and sensitive structures are often located in close proximity, accuracy in the calculation of dose distributions is critically important. The goal of radiation therapy is to deliver a lethal dose to the tumor while maintaining an acceptable dose level in surrounding sensitive structures. This goal is achieved by computer-aided planning of the radiation treatments to be delivered. The treatment planning process consists of characterizing the individual patient's anatomy (most often, this is done using a computed tomography (CT) scan), determining the shape, intensity, and positioning of radiation sources (the subject of the present invention), and calculating the distribution of absorbed radiation dose in the patient. Most current methods used to calculate dose in the body are based on dose measurements made in a water box. Heterogeneities such as bone and airways are treated in an approximate way or ignored altogether. Next to direct measurements, Monte Carlo transport is the most accurate method of determining dose distributions in heterogeneous media. In a Monte Carlo transport method, a computer is used to simulate the passage of particles through an object of interest.

The CREEP single scatter electron Monte Carlo code, the subject of this invention, is designed to be the first phase in a two-part approach to a advanced electron transport package for PEREGRINE. PEREGRINE is an all-particle, first-principles 3D Monte Carlo dose calculation system designed to serve as a dose calculation engine for clinical radiation therapy treatment planning (RTP) systems. By taking advantage of recent advances in low-cost computer commodity hardware, modem symmetric multiprocessor architectures and state-of-the-art Monte Carlo transport algorithms, PEREGRINE performs high-resolution, high accuracy, Monte Carlo RTP calculations in times that are reasonable for clinical use. Because of its speed and simple interface with conventional treatment planning systems, PEREGRINE brings Monte Carlo radiation transport calculations to the clinical RTP desktop environment. PEREGRINE is designed to calculate dose distributions for photon, electron, fast neutron and proton therapy.

The PEREGRINE Monte Carlo dose calculation process depends on four key elements: complete material composition description of the patient as a transport mesh, accurate characterization of the radiation source , first-principles particle transport algorithms (the subject of the present invention), and reliable, self-consistent particle-interaction databases (also an element of the present invention). PEREGRINE uses these elements to provide efficient, accurate Monte Carlo transport calculation for radiation therapy planning.

The patient transport mesh is a Cartesian map of material composition and density determined from the patient's CT scan. Each CT scan pixel is used to identify the atomic composition and density of a corresponding transport mesh voxel. Atomic composition is determined from CT threshold values set by the user or by default values based on user-specified CT numbers for air and water. The user also assigns materials and densities to the interior of contoured structures. If the user specifies a structure as the outer contour of the patient, PEREGRINE constructs a transport mesh that is limited to the maximum extent of that structure, and sets all voxels outside that structure to be air. This provides a simple method of subtracting the CT table from the calculation. The default resolution of the transport mesh is 1×1×3 mm, for small-volume areas such as the head and neck, or 2×2×10 mm, for large-volume treatment sites such as the chest and pelvis. The resolution can also be reduced from the CT scan resolution. For reduced-resolution voxels, material composition and density are determined as the average of all CT pixels that fall within the transport mesh voxel.

The PEREGRINE source model, designed to provide a compact, accurate representation of the radiation source, divides the beam-delivery system into two parts: an accelerator-specific upper portion and a treatment-specific lower part. The accelerator-specific upper portion, consisting of the electron target, flattening filter, primary collimator and monitor chamber is precharacterized based on the machine vendor's model-specific information. These precharacterized sources are derived from Monte Carlo simulations from off-line Monte Carlo simulations using BEAM and MCNP4A, as described in copending U.S. Pat. No. 5,870,697, which is fully incorporated herein by reference. Particle histories from off-line simulations are cast into multidimensional probability distributions, which are sampled during the PEREGRINE calculation. The photon beam is divided into three subsources: primary, scattered, and contaminant. Separating the source into subsources facilitates investigation of the contributions of each individual component. To ensure site-specific model accuracy, the installation procedures will consist of a limited number of beam description parameter adjustments, based on simple beam characterization measurements. The lower portion of the radiation source consists of treatment-specific beam modifiers such as collimators, apertures, blocks, and wedges. This portion is modeled explicitly during each PEREGRINE calculation. Particles are transported through this portion of the source using a pared-down transport scheme. Photons intersecting the collimator jaws are absorbed. Photons intersecting the block or wedge are tracked through the material using the same physical database and methods described below for patient transport. However, all electrons set in motion by photon interactions in the block or wedge are immediately absorbed.

Using the Monte Carlo transport method, PEREGRINE tracks all photons, electrons, positrons and their daughter products through the transport mesh until they reach a specified minimum tracking energy or leave the patient transport mesh. Developing good statistics requires tracking millions of representative particles (histories) through the patient transport mesh. During the simulation, PEREGRINE records energy deposited at each interaction, which builds up a map of energy deposited in the transport mesh. After the Monte Carlo process is finished, a dose map is created by dividing the total energy deposited in each voxel by its material mass. PEREGRINE transports photons through the body using the standard analog method. Woodcock or delta-scattering is used to efficiently track particles through the transport mesh. All photons below 0.1 keV energy are absorbed locally. PEREGRINE transports electrons and positrons using a class II condensed-history scheme. This procedure groups soft collisions with small energy losses or deflections, but simulates directly those major or catastrophic events in which the energy or deflection angle is changed by more than a preset threshold. Delta-ray and bremsstrahlung production are modeled discretely for energy transfers >200 keV. PEREGRINE uses Moliere's theory of multiple elastic electron/positron scattering . Pathlength corrections described are used to account for the effect of multiple scattering on the actual distance traveled by the electron or positron. A minimum electron/positron transport energy is assigned to each transport voxel based on range rejection. The range-rejection minimum energy corresponds to the minimum electrort/positron range required to traverse 20% of the minimum zone dimension, with range determined as the minimum range calculated for that zone plus all directly adjacent zones. Two 511 keV photons are created at the end of each positron range. The direction of the first photon is chosen randomly, while the second is set to 180° opposed to the first.

The accuracy of Monte Carlo dose calculations depends on the availability of reliable, physically-consistent physical databases. For photon/electron/positron transport, PEREGRINE relies on the Lawrence Livermore National Laboratory Evaluated Physical Database, combined with stopping powers supplied by the National Institute of Standards and Technology. CREEP uses the LLNL Evaluated Electron Data Library, which is described in further detail below.

PEREGRINE accounts for photon interactions via the photoelectric effect, incoherent/coherent photon scattering, and pair production. All photon cross sections used by PEREGRINE are derived from the Lawrence Livermore National Laboratory Evaluated Photon Data Library (EPDL). EPDL data are taken from a variety of sources that have been selected for accuracy and consistency over a wide range of photon energies (10-eV-100-MeV) for all elements.

At low incident photon energies (<0.1 MeV for tissue components, <1 MeV for high-Z materials such as lead and tungsten), the photoelectric effect is the dominant absorption mechanism. The cross sections contained in PEREGRINE were obtained by direct evaluation of the relativistic S-matrix in a screened central potential. These cross sections accurately describe ionization from electrons bound in isolated atoms and provide predictions at the percent level for compounds where the K and L shells are well-represented by atomic orbitals. For most elements, at energies typical of those encountered for clinical photon beams, Compton scattering is the most important process in the photon-atom interaction. The Compton scattering cross sections used in PEREGRINE are obtained in the incoherent scattering factor approximation. This approximation includes screening effects. Relativistic effects enter through use of the Klein-Nishina cross section. Coherent scattering does not contribute significantly to the total photon-atom interaction cross section for most radiation therapy applications. However, these cross sections are still modeled, and were obtained under similar assumptions to those for incoherent scattering. At very high incident photon energies (>30 MeV for tissue components, >5 MeV for high-Z materials such as lead and tungsten), the dominant photon interaction mechanism is pair production. The cross sections for pair and triplet production used by PEREGRINE include Coulomb and screening effects and radiative corrections.

PEREGRINE accounts for the effects of large-angle elastic scattering (delta-ray production) and bremsstrahlung production on an event-by-event basis. All other energy-loss mechanisms are accounted for through continuous-slowing-down-approximation (CSDA) energy loss.

Moller (Bhabha) scattering is the ionization of an atom by an electron (positron). Moller and Bhabha cross sections and sampling methods follow those given by Messel and Crawford. The threshold for these processes in PEREGRINE is set so that the ejected electron kinetic energy is >200 keV.

Bremsstrahlung cross sections contained in PEREGRINE are derived from the LLNL Evaluated Electron Data Library (EEDL). These cross sections were determined by interpolating between the relativistic S-matrix data available up to 2 MeV, and the Bethe-Heitler result, expected to be valid above 50 MeV. Bremsstrahlung cross sections are processed to reflect a bremsstrahlung photon energy cutoff of 200 keV. During transport, PEREGRINE uses restricted collision and radiative stopping powers, which exclude energy lost due to Moller/Bhabha events with energy transfers >200 keV and bremsstrahhrng events with energy transfers >200 keV. Restricted collision stopping powers are calculated. Restricted radiative stopping powers are calculated by subtracting the total energy transferred to the bremsstrahlung photon per distance, as determined from the bremsstrahlung cross section data.

The accuracy of PEREGRINE transport calculations has been demonstrated by benchmarking PEREGRINE against a wide range of measurements and well-established Monte Carlo codes such as EGS4 and MCNP. The accuracy of the CREEP-based electron transport package has been demonstrated by comparing PEREGRINE with and without this feature enabled, as well as comparing CREEP results to calorimetric experiments directly, independent of the PEREGRINE code.

SUMMARY OF THE INVENTION

It is an object of the present invention to provide a method for modeling precise microscopic interactions of electrons with matter to enhance physical understanding of radiation sciences.

It is another object of the invention to simulate electrons in any medium, including materials important for biological studies.

Another object of the invention is to provide a method which simulates each electron interaction individually by sampling from a library which contains accurate information over a broad range of energies.

Single scatter physics is gaining attention for electron transport, despite the fact that it is inherently very time consuming. One reason is that since single scatter calculations conform (more) closely to the physical processes the electron undergoes, they can serve as a means to explore the validity of assumptions used in other transport techniques. In particular, single scattering can help make efficient electron transport methods, like condensed history and local-to-global methods, more accurate. SSMC allows large angle scatter and backscatter measurements to be calculated with greater accuracy in a reliable manner. Large angle scatter and backscatter, being relatively rare, result in much of the seemingly eccentric energy deposition behavior of electron beams (and photon beams for that matter, since photons deposit their energy to the medium through secondary electrons), including lateral blooming with distance and nonuniformities ("hot" or "cold" spots) found near changes in the medium type or density.

The Evaluated Electron Data Library (EEDL) was established at LLNL to complement the Evaluated Nuclear Data Library (ENDL) and Evaluated Photon Data Library (EPDL). Cross sections for each atomic subshell, for each interaction, are tabulated on an energy grid with a variable placement of points between 10 eV and 100 GeV, for atomic numbers 1 to 100. The elastic scattering cross sections are based on those of Mott for energies greater than 256 keV and of Riley below 256 keV. These data were then extrapolated to cover the entire energy range. Spectra, in the form of probability distribution functions (PDFs), of angular deflections for a variety of incident energies are also tabulated.

The impact ionization cross sections are based on the Moller formalism with other corrections to accurately model small energy loss collisions. Energy loss spectra are available at a number of incident energies for individual ionization and bremsstrahlung events, as well as the spectral average energy loss.

The bremsstrahlung cross sections were determined by Seltzer and Berger by interpolating between the relativistic data from the code of Tseng and Pratt available up to 2 MeV, and the results of Bethe-Heitler, expected to be valid above 50 MeV. The excitation database contains cross sections and the average energy loss to excitation as a function of incident energy. There are no spectral data for excitation energy loss in EEDL at this time.

The CREEP code is written in FORTRAN and C, in a very simple style with the intent of being extremely portable. Since this code is intended primarily as a means to explore basic physical properties of the medium, the present incarnation assumes only simple geometries: either spherical (user specifies radius) or slab (user specifies x, y, z), consisting of one type of material. Several slabs may be pieced together to simulate a layered geometry, since the output of one slab may be used as spectral input into a distal slab, and the backscattered energy spectrum from each interface can be transported backwards in the prior medium.

DETAILED DESCRIPTION OF THE INVENTION

Figure 4:
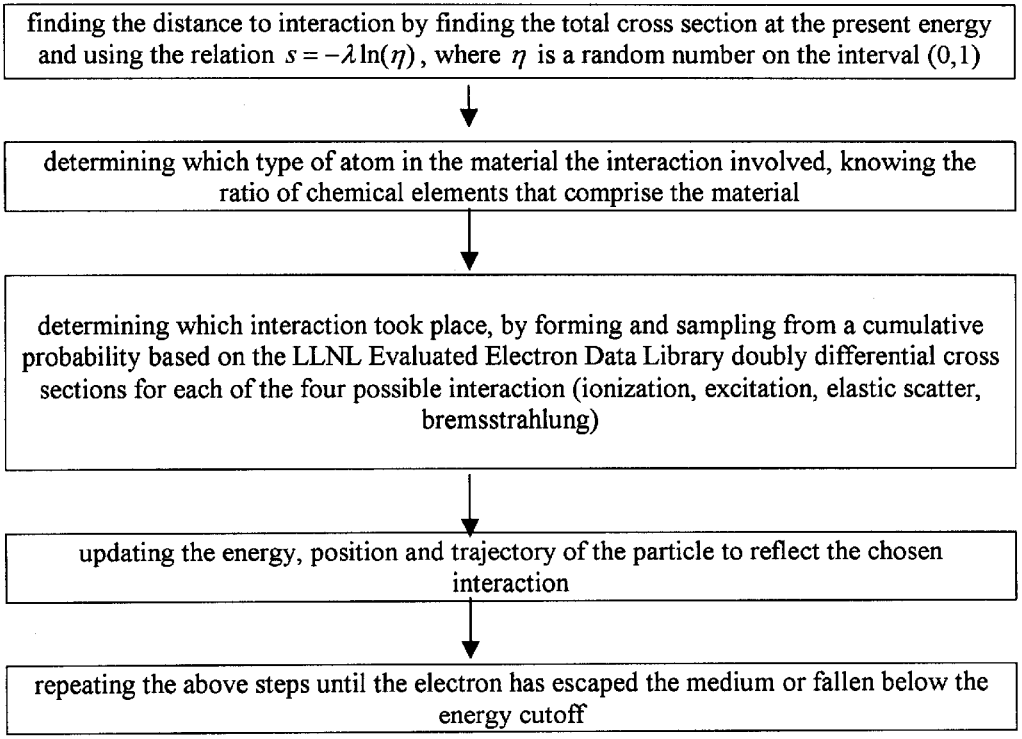
FIG. 4 shows the algorithm for the single scatter charged particle code of the present invention.
Figure 5:
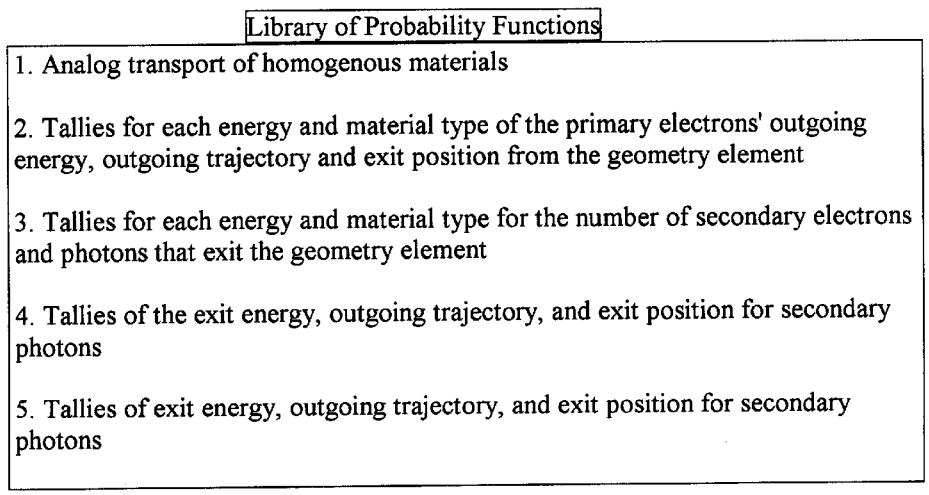
FIG. 5 shows the library of probability functions used in the present invention.

CREEP is able to obtain its accuracy by simulating electron events in an "analog" or "single scatter" fashion. The overall algorithm for a truly single scatter charged particle code, as shown in FIG. 4, is a direct analog of the algorithm that has historically been used in photon and neutron Monte Carlo codes. Briefly, one finds the distance to interaction by finding the total cross section at the present energy and uses the relation $s=-\lambda \ln(\eta)$, where $\eta$ is a random number on the interval (0,1). One then determines which interaction took place, by forming and sampling from a cumulative probability based on the cross sections for each of the four possible interactions (ionization, excitation, elastic scatter, bremsstrahlung). The energy, position and trajectory of the particle is updated to reflect the chosen interaction in a manner described for each below, as shown in FIG. 5. Then the same process is begun again, provided the electron has not escaped the medium or fallen below the energy cutoff.

CREEP is actually a family of four codes, having a similar ancestor code, but they have evolved separately to fill specific niches. SlabcreepI, was written for the purpose of benchmarking with slab and foil experiments. SlabcreepII does the same but for media that are not comprised of a single element; it handles compounds and mixtures and was primarily designed as a means to compare the CREEP method with other codes and experiments for generating depth-dose curves in water, which is the most important medium for radiotherapy applications. The ultimate application for CREEP was to generate a library for the Macro Response Method (MRMC), for which probability distribution functions arising from transport through a sphere were required. Thus KugcreepI and KugcreepII were born; the former for single-element materials and the latter for compounds and mixtures in spherical geometry. It would have been possible to merge the codes, however, the decision was made to keep them separate in the interest of efficiency.

For both the slab-geometry code and the spherical-geometry kugel code, there are two types of input files. The first is a very simple user-generated file explaining the Monte Carlo tracking parameters, the medium, and the output information desired. The second type of information files required is the EEDL datafiles for each element in the medium. The CREEP code deviates from the ideal single scatter algorithm in that (for most applications) it does not simulate every excitation event individually. Instead, it subtracts off the expected excitation loss after each of the other events, as described in the excitation section below. This choice was made because it was felt that there was little to gain by direct simulation of excitations, since they do not have a large effect on the electron trajectory, and the amount of the overall energy loss to this mechanism—although it can be large—doesn't vary much. By definition there are no orbital electrons that receive enough energy to be liberated (because this is ionization) however, it is possible that low-energy Auger electrons and/or fluorescent photons will be generated as the atom relaxes; these are neglected. However, since the excitation cross section is large, much simulation time is devoted to this very small gain in accuracy.

Ionization interactions are generally the dominant energy loss mechanism for electrons slowing down from the radiotherapy energy range. They occur when a charged particle imparts enough of its kinetic energy to a orbital electron to set that electron free. Once the electron is free it is called a "knock-on" electron or "delta-ray". For incident electrons, the interaction is often pictured as a "black box" in the vicinity of an atomic electron, where two electrons exit. Because electrons are indistinguishable from each other, it is simply assumed that the electron with the higher exit energy was the primary electron, making the remaining electron the "knock-on". With this definition, the maximum energy a knock-on electron can have is given by $$T'_{knock,max} = \frac{T_0 - E_{bind}}{2}. \quad (2.1)$$

To simulate an ionization interaction, the knock-on electron energy is sampled from a spectrum. The EEDL database has a number of spectra tallied for various incident energies; statistical interpolation is used to choose between them. Once the energy of the knock-on has been selected, 2-body kinematics (neglecting binding energy) are used to update the primary electron's trajectory. If $T_0$ is the kinetic energy of the electron in electron mass units, and the ratio $\chi$ is defined by $$X = \frac{T_{knockon}}{T_0},$$

then the outgoing angles are given by $$\cos\theta_{pri} = \sqrt{\frac{\chi(T_0+2)}{(\chi T_0)+2}} \quad (2.2)$$

and for the knock-on electron $$\cos\theta_{knock} = \sqrt{\frac{(1-\chi)(T_0+2)}{((1-\chi)T_0)+2}}, \quad (2.3)$$

Note that because the binding energy is neglected, these angles are less valid at energies near it. Since such electrons don't travel far, this assumption does not have a large impact on the overall transport results.

CREEP handles secondary electrons by putting the primary on a memory "stack" and tracking the knock-on immediately, until they fall below the energy cutoff or escape the volume, at which point the primary history is continued. A special energy cutoff parameter is used for knock-ons, so the user can readily imitate class II condensed history codes, which only simulate ionization events if the knock-on is above a particular energy.

Presently it is assumed that all binding energy is locally deposited. However, this assumption is known to be somewhat weak since significant fractions of the binding energy may be re-emitted as Auger electrons or fluorescent x-rays. While the Auger electrons do not travel far, many of the x-rays are emitted at energies that fall just below the photoelectric edges, where the cross-sections are small and they can therefore carry their energy relatively far from the interaction site. Another LLNL database, the Evaluated Atomic Data Library (EADL) contains all the necessary information to model these relaxations physically, but is not incorporated into the code at this time.

In elastic scatter interactions, an incident electron traveling in the vicinity of a nucleus scatters off the nucleus at some angle without a significant loss in energy, due to the large mass difference between the two. However, each scatter does cause a modest angular deflection. Due to its large cross-section, the net effect of elastic scatter on a particle's trajectory can be very significant indeed.

The cross section for elastic scatter as a function of solid angle is given by the McKinley-Feshback form of Mott scattering in the expression $$\frac{d\sigma_{elas}}{d\Omega} = \frac{Z^2}{4}\left(\frac{e^2}{m_0 c^2}\right)^2 \frac{1-\beta^2}{\beta^4} \frac{1}{\sin^4(\theta/2)} \times \quad (2.4)$$
$$\left[1 - \beta^2 \sin^2(\theta/2) + \pi\beta\frac{Z}{137}(1-\sin(\theta/2))\sin(\theta/2)\right],$$

where Z is the nuclear charge, and the term outside of the square brackets is the Rutherford scattering term. Note that the cross section depends inversely on the square of the rest mass of the particle, so heavy charged particles, like protons or ions, scatter much less than electrons and positrons.

To simulate this event, one samples a scattered angle from EEDL (where it is tabulated as $1-\mu;\mu$ being the cosine of the scattered angle) and updates the trajectory. Although most elastic scattering results in only a small angle, it is this mechanism that is almost exclusively responsible for the phenomena of backscatter and large angle scatter.

Bremsstrahlung interactions occur when the electron passes near the nucleus and accelerates due to the interaction of their Coulomb fields, causing a photon to be emitted. Although low energy photons are more likely, an electron can lose up to all of its energy to the photon. As an energetic charged particle of mass $m_0$. and charge ze passes in the vicinity of a nucleus of mass $M_n$. and charge Ze, there will be an electrostatic force between the two particles due to the interaction of the Coulomb fields, given by $$F_E = \frac{kzZe^2}{r^2}. \quad (2.5)$$

The incident charged particle will experience an acceleration due to this force of magnitude $$a = \frac{kzZe^2}{r^2 m_0}, \quad (2.6)$$

where r is the separation between the particles and k is a fundamental electromagnetic constant=$(4\pi\epsilon_0)^{-1}$. Assuming the mass of the charged particle is small compared to the nucleus, the nucleus does not move significantly as a result of the force in equation (2.5). However, the force will cause the charged particle to be deflected from its path and momentarily orbit around the nucleus. An accelerated charge radiates energy at a rate proportional to the square of its acceleration $$\left.\frac{dT}{dt}\right|_{brem} \propto \left(\frac{kzZe^2}{r^2 m_0}\right)^2, \quad (2.7)$$

Equation (2.5) illustrates several important concepts governing bremsstrahlung emission. First, it is apparent that it is much more common for light particles such as electrons to emit photons than it is for heavier particles like protons, due to the $1/m_0^2$ dependency. Secondly, it can be seen that bremsstrahlung is much more important in high atomic number materials (due to the $Z^2$) than in low atomic number materials. In principle, it is possible to have bremsstrahlung created in the field of an atomic electron, but the probability is much lower, since the charge (and therefore the acceleration) is less.

The basic dependencies shown in equation (2.5) may be $$x = \frac{T_0 \theta_0}{m_0 c^2};$$

expressed in terms of a reduced angle, $$\sigma_b(k, x) = \frac{4Z^2}{137} \left(\frac{e^2}{m_0 c^2}\right)^2 \frac{dk}{k} x dx \left\{\frac{16x^2 T}{(x^2+1)^4 T_0} - \right. \quad (2.8)$$
$$\left. \frac{(T_0+E)^2}{(x^2+1)^2 T_0^2} + \left[\frac{T_0^2 + T^2}{(x^2+1)^2 T_0^2} - \frac{4x^2 T}{(x^2+1)^4 T_0}\right] \ln M(x)\right\},$$

where $$\frac{1}{M(x)} = \left(\frac{m_0 c^2 k}{2T_0 T}\right)^2 + \left(\frac{Z^{1/3}}{111(x^2+1)}\right)^2, \quad (2.9)$$

and $k=hv=T_0-T$, the energy of the bremsstrahlung photon.

The exact rate of energy loss by bremsstrahlung depends on the quantum mechanical nature of this interaction, which is beyond the scope of this disclosure. However, for energies less than 100 MeV, the energy loss may be estimated by the equation $$\frac{1}{\rho}\left(\frac{dT}{dx}\right)_{rad} = 4r_0^2 \frac{N_e ZT}{137}\left[\ln\frac{2(T+m_0 c^2)}{m_0 c^2} - \frac{1}{3}\right], \quad (2.10)$$

where $N_e$ is the number of electrons per gram, T is the kinetic energy of the electron, and $r_0$ is the classical electron radius ($r_0 = 2.81794 \times 10^{-15}$ m). The important physics revealed by this equation is that energy loss increases directly with atomic number of the material, and the loss increases to a somewhat greater extent with the energy of the electron.

In bremsstrahlung interactions, the initial momentum of the incident particle becomes shared between the scattered charged particle, the atomic nucleus and the emitted photon. Therefore the photon can have any energy up to $hv_{max}=T$. In this manner charged particles, especially electrons, have a small probability of losing almost all of their energy in a single interaction, however, this only occurs at extreme relativistic energies. At extreme relativistic energies, both the photon and the scattered charged particle advance preferentially in the forward direction. For moderate energy charged particles, however, the photon carries only a very small momentum and can be emitted in any direction.

In CREEP, the photon energy is sampled from a spectrum, and an empirical relation can be used to determine the angle of the electron after interaction:

$$\mu = 1 - \left(\frac{m_0 c^2}{K_0 - hv} - \frac{m_0 c^2}{K_0}\right). \quad (2.11)$$

The "birth" angle of the bremsstrahlung photon is more difficult; it is most correctly obtained by sampling the Schiff formula, but CREEP uses the approximation $$\theta = \frac{m_0 c^2}{m_0 c^2 + K_0} \quad (2.12)$$

where the denominator represents the total energy of the electron before the event.

CREEP itself does not track the bremsstrahlung photons that are created; they are tallied on the spot so that their phase space can be banked and passed off to another Monte Carlo code with photon tracking capabilities, such as PEREGRINE. Note that any additional electrons the bremsstrahlung photons would have generated are "lost", so CREEP cannot assume any energy deposits arising from photons. If, however, CREEP is coupled with a photon MC code in a way that allows that code to pass back further secondary electrons these can be restored. It should be noted that the bremsstrahlung photon is much more penetrating than the charged particle that caused it, and therefore carries its energy far from the original charged particle track. Monte Carlo codes that neglect bremsstrahlung interactions thus fail to model this energy deposition pattern accurately.

The primary charged particle can excite an atom even thought it does not impart enough energy to the atomic electron to free it. Instead, the energy transferred to the atom causes the orbital electron to be promoted to a higher electronic state. The promoted orbital electron relaxes either by producing characteristic (photon) radiation of energy hv; producing Auger electrons of energy $hv-E_{binding}$; or some combination of both. Since the energies involved are typically very low compared to the energy range of interest, the individual events are often not modeled and the energy that is given to them is instead considered to be locally deposited. In fact, these events may be lumped together and assumed to cause a uniform energy loss per unit distance. This is an "excitation-only" stopping power.

In CREEP, the energy loss due to excitations can be accounted for by finding the total excitation cross section at current energy, and using the mean energy lost to excitation events at that energy to construct an excitation-only stopping power through the relation $$\left(\frac{dE}{dx}\right)_{ex} = \frac{N_A}{A} \rho \sigma_{ex} \overline{\epsilon_{ex}} \quad (2.13)$$

where $N_A$ is Avogadro's number, A is the atomic weight, $\rho$ is the density, $\sigma_{ex}$ is the total excitation cross section (summed over all subshells), and $\overline{\epsilon_{ex}}$ is the mean energy loss due to excitation at a given primary energy. This stopping power is multiplied by the distance between the last event and the present event to get the energy lost to excitations in transit, which is subtracted from the electron's energy before calculating the distance to the next event.

Another option for modeling excitation is to treat it in the same analog manner as the other interactions. In this case, the excitation cross section is summed into the cumulative event probability function and chosen accordingly. There is no deflection angle, and, rather than sampling from a spectrum of possible energy losses, the average energy loss per event (for an electron of the current energy) is used.

A special version of the CREEP code handles all compounds and mixtures by combining the EEDL element data using Bragg additivity. The user must enter mass fractions of each element in the compound or mixture. The density used is that for the compound as a whole. This simple approach does not account for any chemical binding effects, which start to become important near the binding energy of the medium. The algorithm is the same as that described in the beginning of the previous discussion for elements, except that once the distance to the next interaction is found, the next step is to select which medium the electron will interact with (by comparing a random number to their mass-fraction weighted cross sections) and then selecting the type of interaction as usual within that medium.

Benchmarking of this code with experiment for a variety of elements and select compounds and mixtures, over the energy range of the EEDL database, is a large effort that is still in its infancy. There are many possible outputs of this code to be analyzed; some of which can be readily compared to experiments and theoretical models. Other information has no feasible experimental equivalent and as such is of interest primarily in a qualitative sense (such as "event maps" which plot interaction sites for all types of interactions). A few examples of both quantitative and qualitative results are shown in the remainder of this section. electrons escape without losing at least some energy. This region ends abruptly at the energy loss that corresponds to the excitation-only stopping power times the thickness of the slab, where a sharp peak is seen. The peaks are due to electrons that escape the slab without undergoing any ionization (or bremsstrahlung) events. The sharpness of these peaks is therefore an artifact resulting from not modeling individual excitation events.

The next distinctive feature of these curves is a gap of low amplitude following the peak. This discontinuity is due to the binding energy of the material, which, for gold (Z=79) is 8.3 eV and for tantalum (Z=73) is 7.31 eV. If an electron doesn't escape without ionization, it must give up the binding energy (in this code locally deposited in the medium), which explains the lack of electrons seen until the low, broad peak. The shoulder on the large-energy-loss side of this peak rolls off very gradually, as there is progressively smaller probability of multiple ionization events and/or single large energy loss events.

Comparisons of the CREEP single scatter Monte Carlo (SSMC) code with experiment are shown in FIGS. 3A–G Agreement to experiment is generally quite good for a variety of materials, incident energies, and incident angles. The curves did not require normalization. Energy deposition is shown as a function of depth into the medium, where the depth has been normalized to the CSDA range of the electron in each case. The points attributed to Lockwood et al. are from calorimetric measurement; the comparisons are absolute.

Figure 1A:
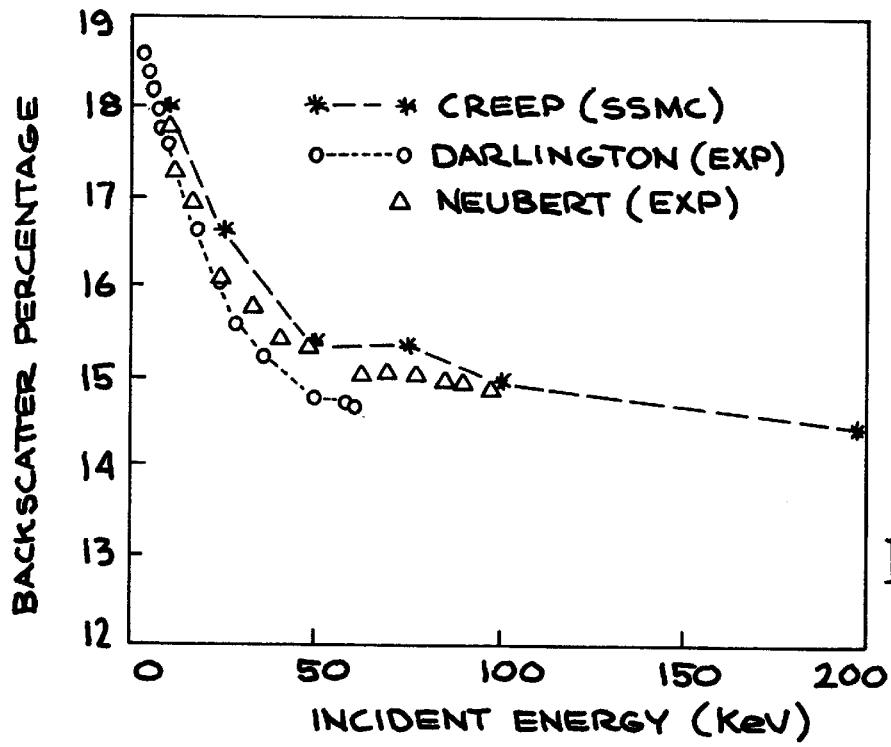
FIGS. 1A and 1B show two examples of backscatter information generated by CREEP compared to experimental values.
Figure 1B:
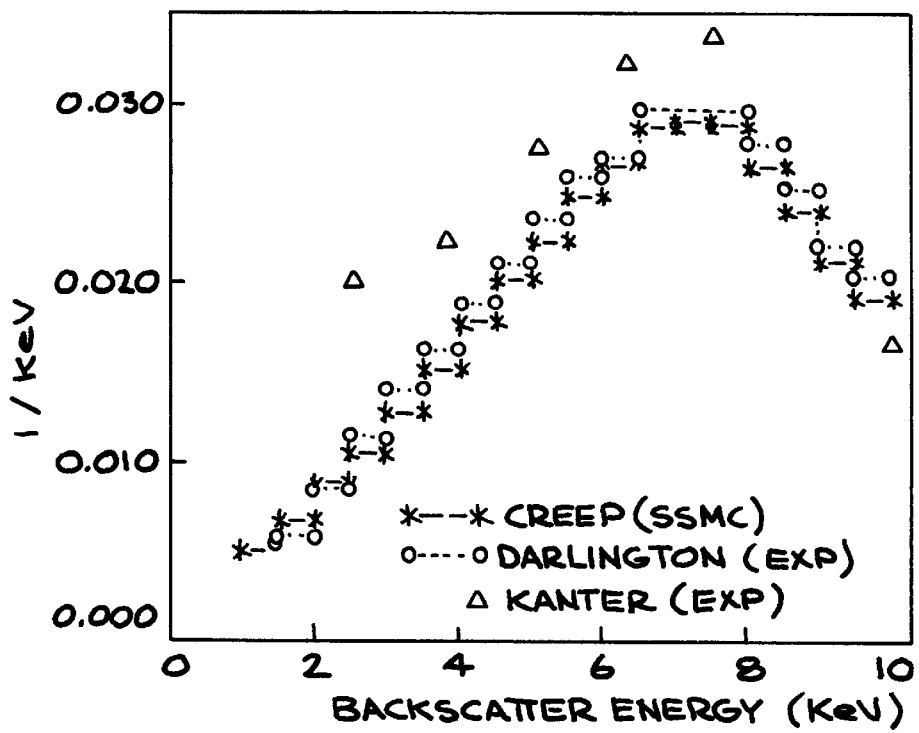

In addition to the preceding quantities, CREEP also calculates analog stopping powers (the amount of energy lost per unit distance Historically, backscatter has been difficult for condensed history codes to simulate correctly. FIGS. 1A and 1B show two examples of backscatter information generated by CREEP compared to experimental values. The agreement is generally quite good. FIG. 1A shows CREEP backscatter percentage (including backscattered secondary electrons) compared to the experiments of Darlington et al. and Neubert et al. FIG. 1B shows the backscattered energy spectrum resulting from a 10 keV electron impinging on the surface of an aluminum slab that is large in x, y, and z compared to the mean free path of the incident electron.

Figure 2A:
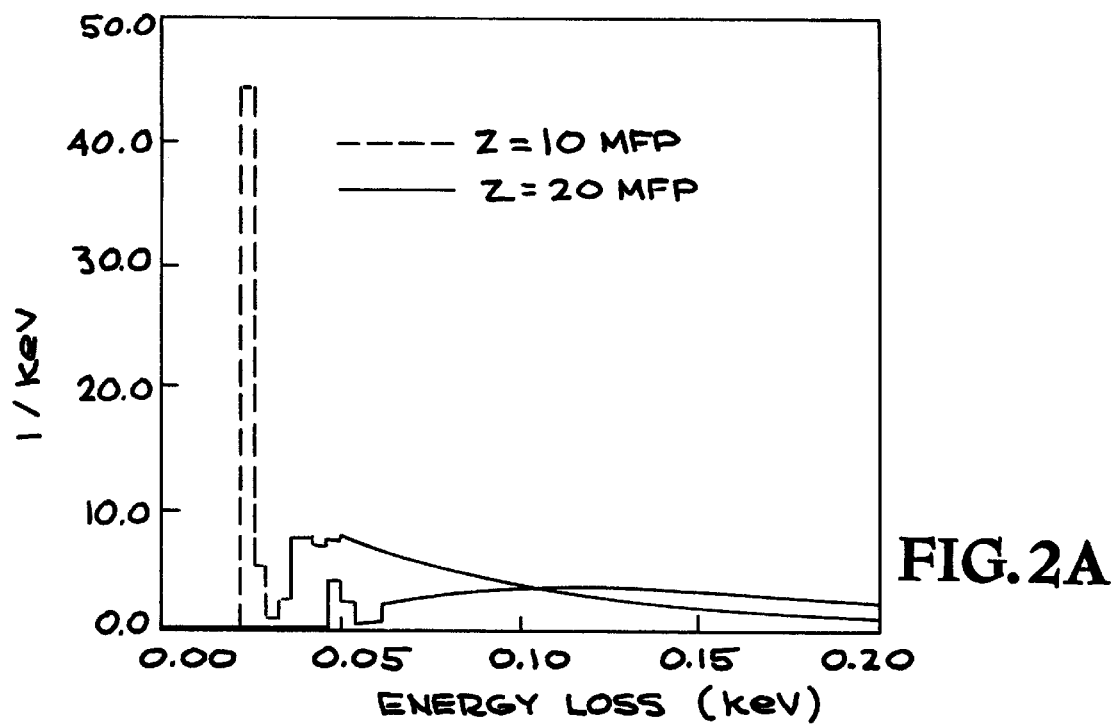
FIGS. 2A and 2B strikingly illustrate both the strengths and the limitations of the present version of CREEP.
Figure 2B:
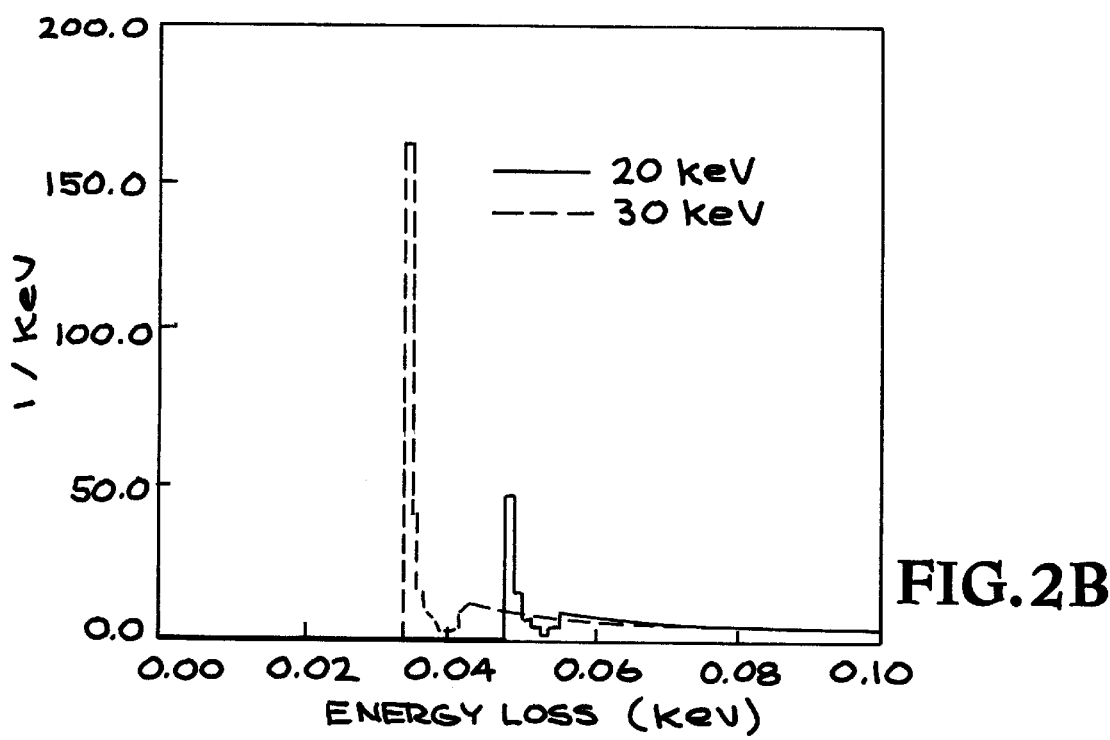
Figure 3A:
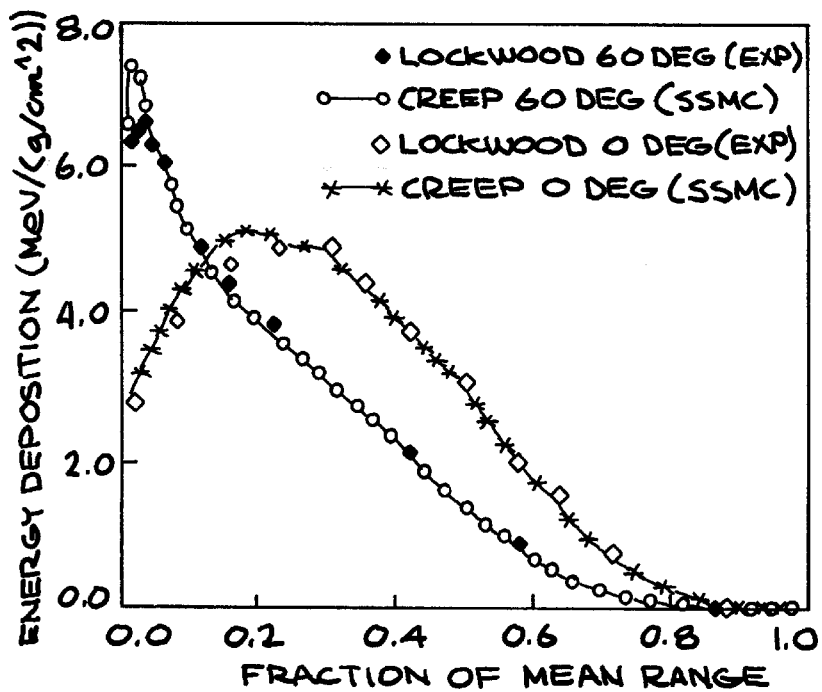
FIGS. 3A–G show comparisons of the CREEP single scatter Monte Carlo (SSMC) code with experiment.
Figure 3B:
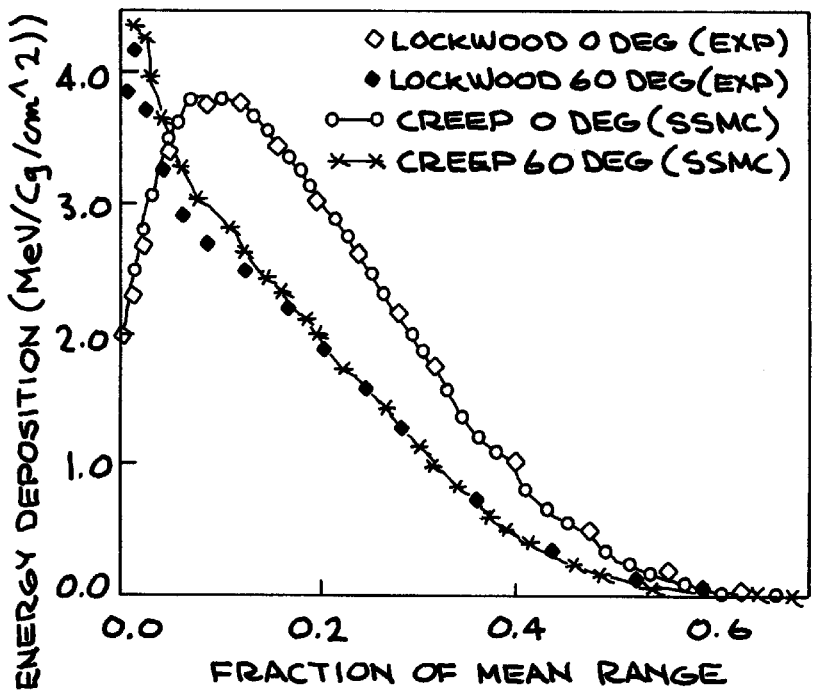
Figure 3C:
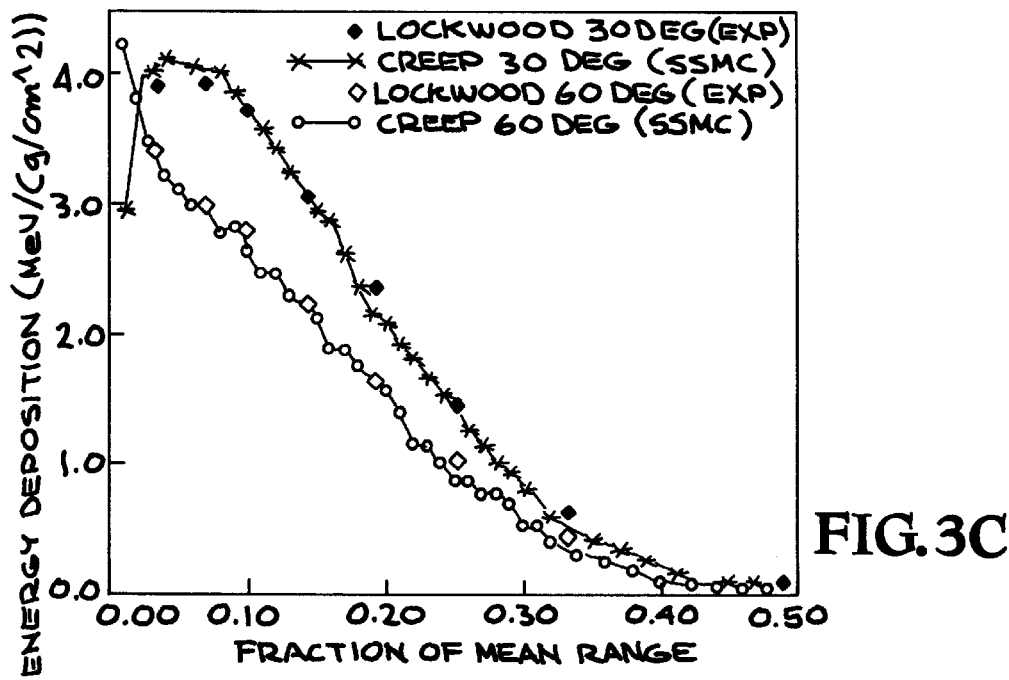
Figure 3D:
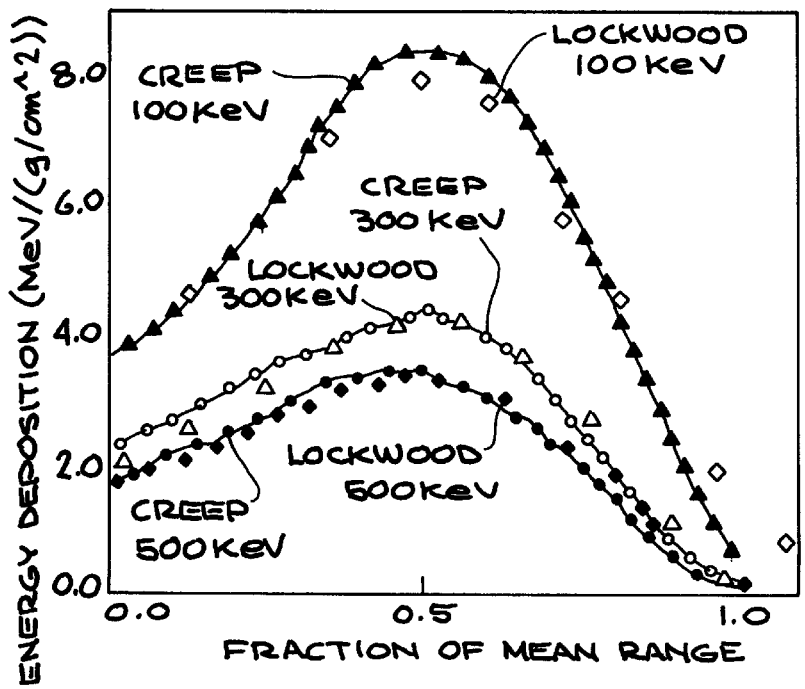
Figure 3E:
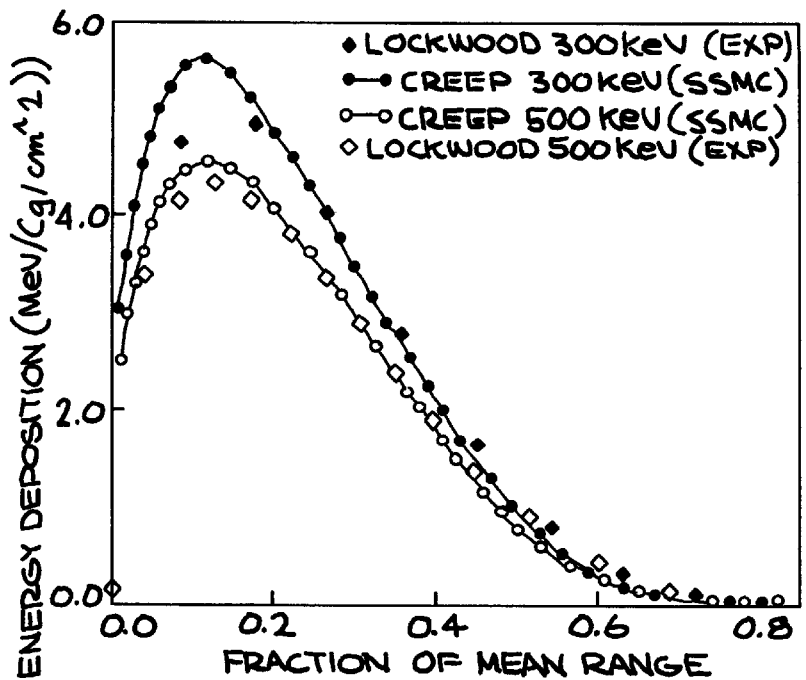
Figure 3F:
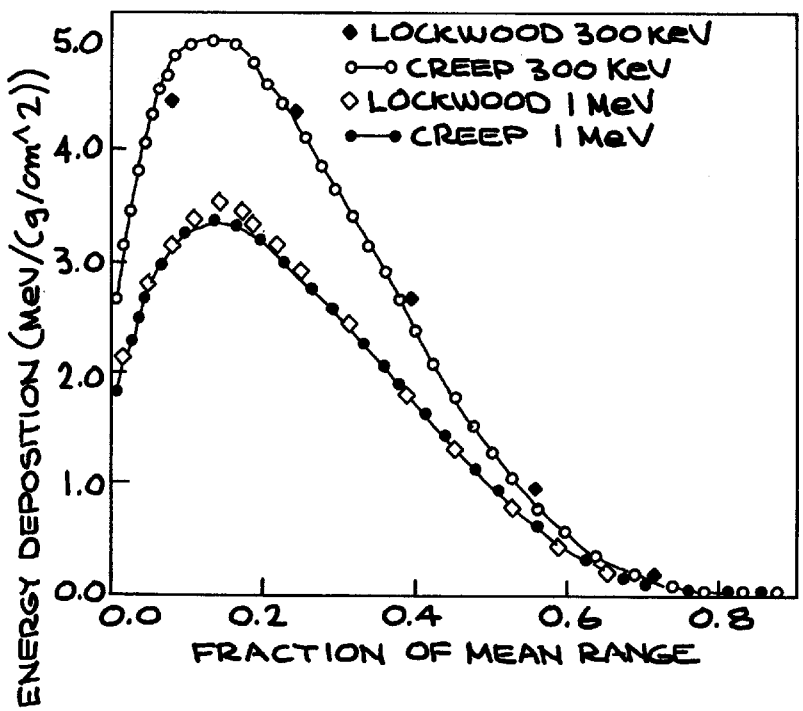
Figure 3G:
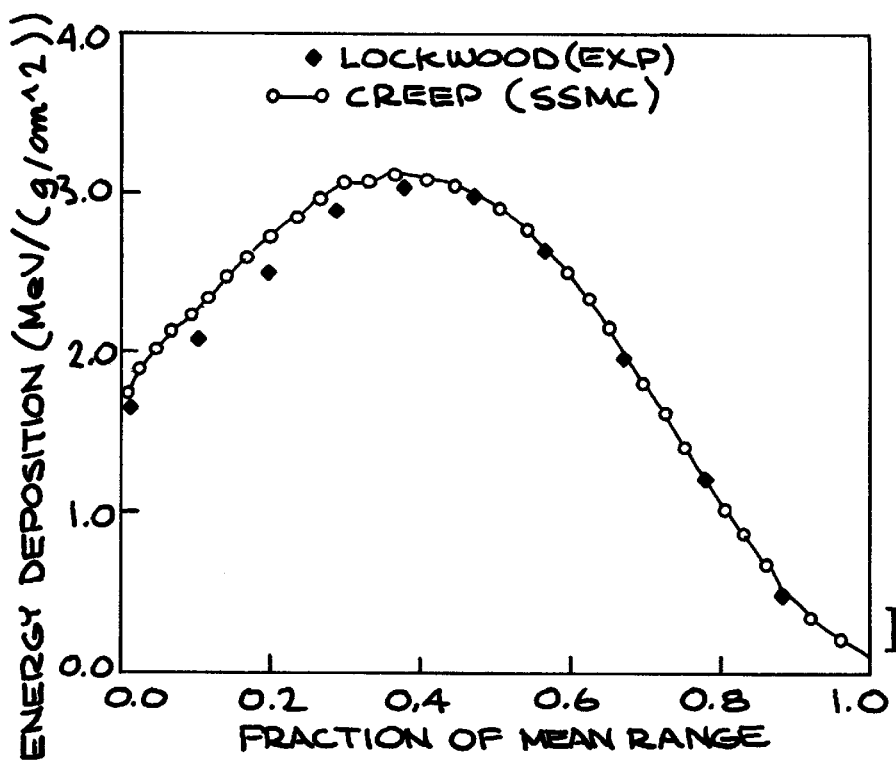

FIGS. 2A and 2B strikingly illustrate both the strengths and the limitations of the present version of CREEP. For each of the four curves shown, an electron of relatively low energy (not more than 500 times the binding energy) is incident on a thin slab (not more than 20 mean free paths) and the amount of energy each electron lost after having traversed the slab is tallied. Although a Landau energy loss distribution (the basis for energy loss in some condensed history codes) would predict a wide, smooth distribution, SSMC gives a highly structured, asymmetric distribution, having the same mean. FIG. 2A shows the exiting energy loss spectra after 32 keV electrons are transmitted through gold (Z=79) slabs of two different thicknesses: $2.87 \times 10^{-6}$ cm (approximately 10 mean free paths) and $5.74 \times 10^{-6}$ cm (approximately 20 mean free paths). FIG. 2B shows the same in tantalum (Z=73) for a constant thickness of $3.0 \times 10^{-6}$ cm at two different energies.

The first distinctive feature of these curves is a zero-amplitude region in the low energy loss region, implying that no for both radiative and collisional events), energy deposits due to individual interaction types, and "real" pathlength (cumulative distance between events) which can be used to calculate detour factors (the ratio to the real range compared to the CSDA range).

Single scatter electron transport is time consuming. This method is not intended to be a general-purpose means of electron transport, but rather a powerful tool for use in situations where it is desirable to obtain information about the basic interaction of electrons with the medium. In general, the simulation time increases with the number of histories, the geometry size, and as the energy threshold is lowered. All of these require more interactions to be simulated. The version of the code which includes compounds and mixtures is also notably slower than the element versions, due to the need to find cross sections in each element for every step, and then compare them to decide in which element the interaction will take place. It is clear that these times are not acceptable for clinical radiotherapy calculations. For this reason, one important application of this code is to compile the results of detailed runs in small geometry elements of homogenous materials. The results are stored in a library of probability distribution functions, which can later be used to represent the net effect of many individual interactions in a single step.

Changes and modifications in the specifically described embodiments can be carried out without departing from the scope of the invention, which is intended to be limited by the scope of the appended claims.

What is claimed is:

1. A method for modeling precise analog microscopic interactions of electrons with matter, comprising:
   finding the distance to interaction by finding the total cross section at the present energy and using the relation $s=-\lambda \ln(\eta)$, where $\eta$ is a random number on the interval (0,1);
   determining which type of atom in the material the interaction involved, knowing the ratio of chemical elements that comprise the material;
   determining which interaction took place, by forming and sampling from a cumulative probability based on the LLNL Evaluated Electron Data Library doubly differential cross sections for each of the four possible interactions (ionization, excitation, elastic scatter, bremsstrahlung);

updating the energy, position and trajectory of the particle to reflect the chosen interaction; and repeating the above steps until the electron has escaped the medium or fallen below the energy cutoff.

2. The method of claim 1, further comprising compiling a library of probability distribution functions representing the net effect of the many interactions on the outgoing electrons' energy, trajectory, and position, wherein said library comprises:

analog transport in small volumes of homogenous materials for a variety of incident energies from approximately 0.01 MeV to 50 MeV;

tallies for each energy and material type of the primary electrons' outgoing energy, outgoing trajectory and exit position from the geometry element;

tallies for each energy and material type for the number of secondary electrons and photons that exit the geometry element;

tallies of the exit energy, outgoing trajectory, and exit position for secondary electrons; and tallies of the exit energy, outgoing trajectory, and exit position for secondary photons.

* * * * *